United States Patent [19]

Stanners

[11] Patent Number: 5,403,288
[45] Date of Patent: Apr. 4, 1995

[54] SAFETY SLEEVE FOR DENTAL SYRINGE

[76] Inventor: Sydney D. Stanners, #1 - 930 Pemberton Road, Victoria, B.C., Canada, V8S 3R4

[21] Appl. No.: 834,854

[22] Filed: Feb. 13, 1992

[51] Int. Cl.⁶ ............................................. A61M 5/00
[52] U.S. Cl. .................................. 604/232; 604/110; 604/197; 604/228; 604/240; 604/241
[58] Field of Search ............... 604/218, 232, 234, 110, 604/195, 197, 228, 240, 241, 198; 206/363–368

[56] References Cited

U.S. PATENT DOCUMENTS

| | | | |
|---|---|---|---|
| 3,008,570 | 11/1961 | Roehr et al. | 604/197 |
| 3,292,776 | 12/1966 | Penn | 206/366 |
| 3,783,997 | 1/1974 | Brown | 206/365 |
| 3,820,652 | 6/1974 | Thackston | 206/365 |
| 4,425,120 | 1/1984 | Sampson et al. | |
| 4,573,976 | 3/1986 | Sampson et al. | |
| 4,631,057 | 12/1986 | Mitchell | |
| 4,655,751 | 4/1987 | Harbaugh | |
| 4,826,490 | 5/1989 | Byrne et al. | |
| 4,859,182 | 8/1989 | Nerli | |
| 4,898,590 | 2/1990 | Andors | |
| 4,907,968 | 3/1990 | Elsner | |
| 4,915,702 | 4/1990 | Haber | |
| 4,931,040 | 6/1990 | Haber et al. | 604/110 |
| 4,935,014 | 6/1990 | Haber | 604/110 |
| 5,088,988 | 2/1992 | Talonn et al. | 604/198 |
| 5,112,307 | 5/1992 | Haber et al. | 604/240 |
| 5,122,124 | 6/1992 | Novacek et al. | 604/110 |
| 5,161,681 | 11/1992 | Kemp et al. | 206/364 |
| 5,176,657 | 1/1993 | Shields | 604/232 |
| 5,188,617 | 2/1993 | Linder | 604/232 |
| 5,195,985 | 3/1993 | Hall | 604/232 |

Primary Examiner—C. Fred Rosenbaum
Assistant Examiner—Ron Stright, Jr.
Attorney, Agent, or Firm—Oyen Wiggs Green & Mutala

[57] ABSTRACT

This invention relates to a safety dental syringe which before and after use protects the needle from exposure. More particularly, this invention pertains to a safety sleeve for a conventional dental syringe wherein after the syringe is used, an overlying sleeve surrounding the barrel of the syringe is extended so that the exposed used needle of the syringe is shielded by the sleeve. The invention pertains to a needle and sleeve assembly useful for use in association with a dental syringe comprising a hollow barrel, a piston, and an anaesthetic ampule cavity therein, comprising: a hollow elongated sleeve having openings at each end thereof; and a hollow housing base which supports at one end thereof an injection needle, and at the other end thereof, an ampule penetrating needle, the exterior of the housing base being adapted to slidably engage with the hollow interior of the sleeve.

15 Claims, 7 Drawing Sheets

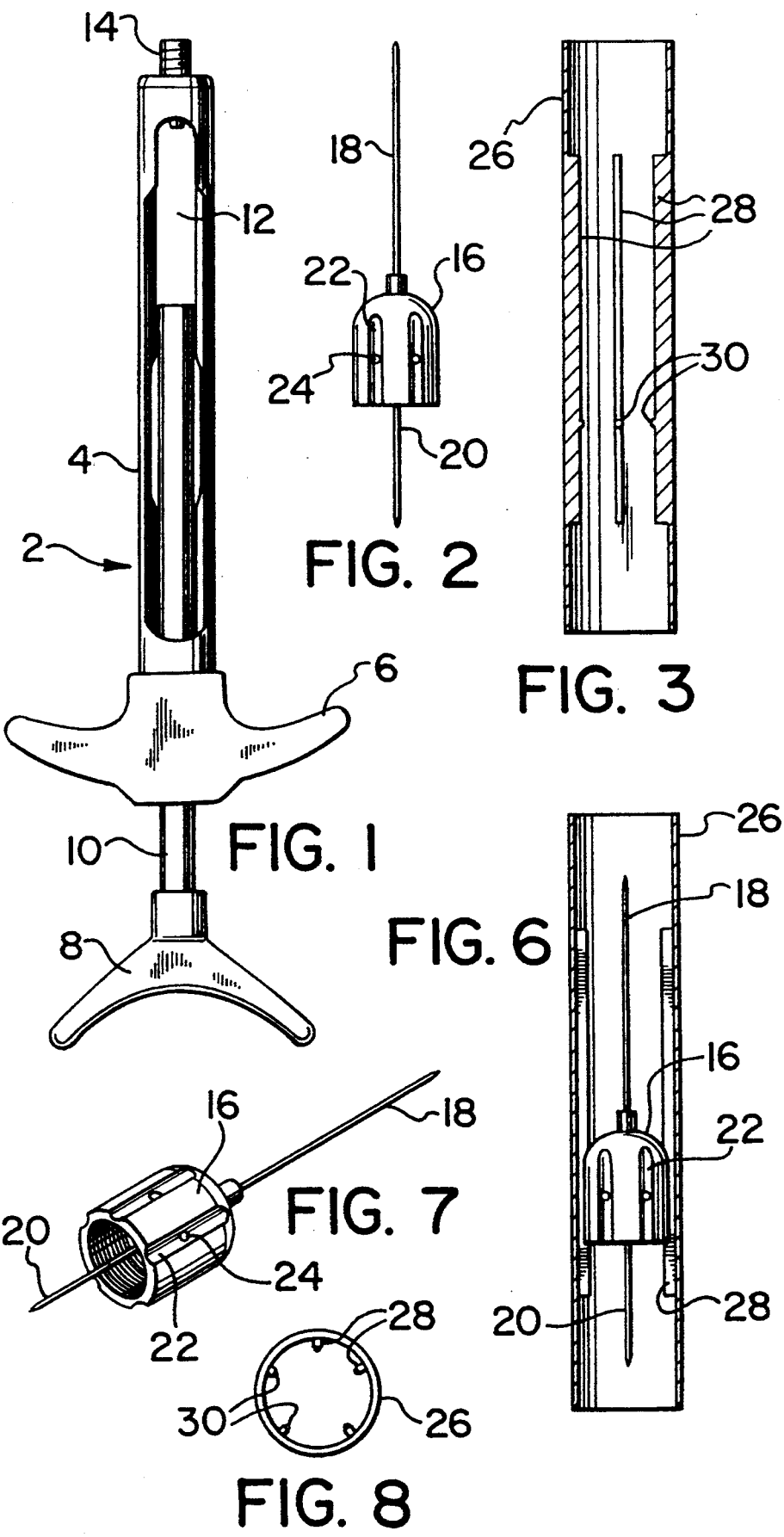

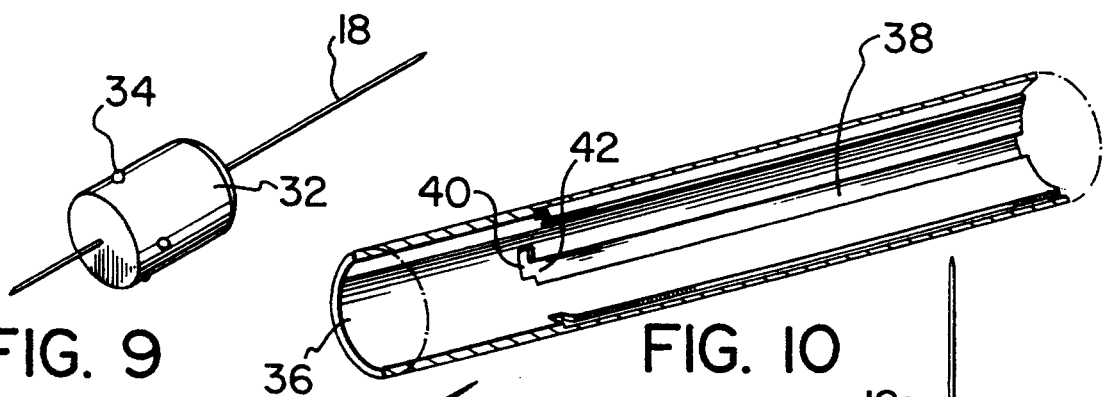
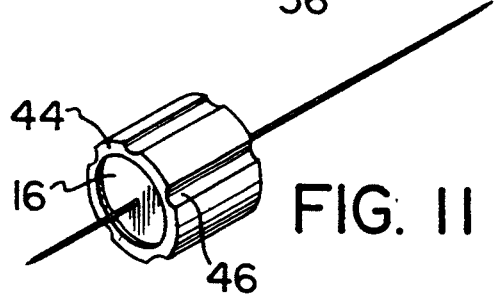
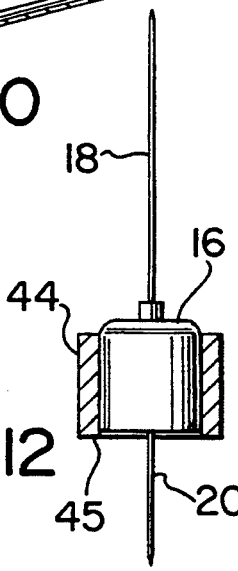
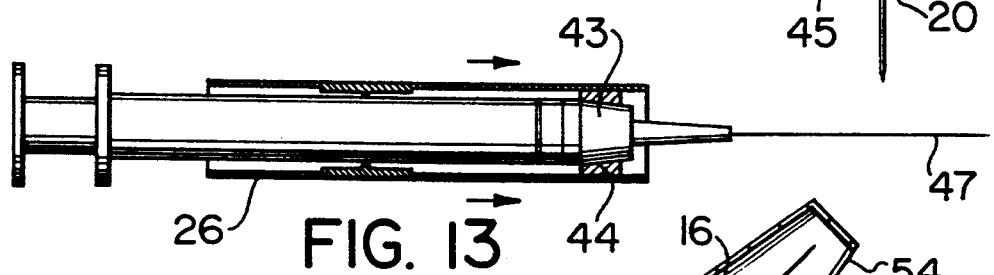
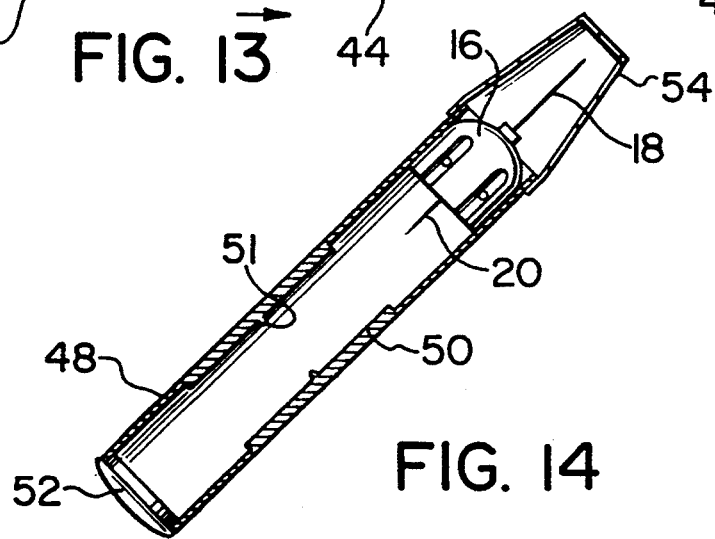

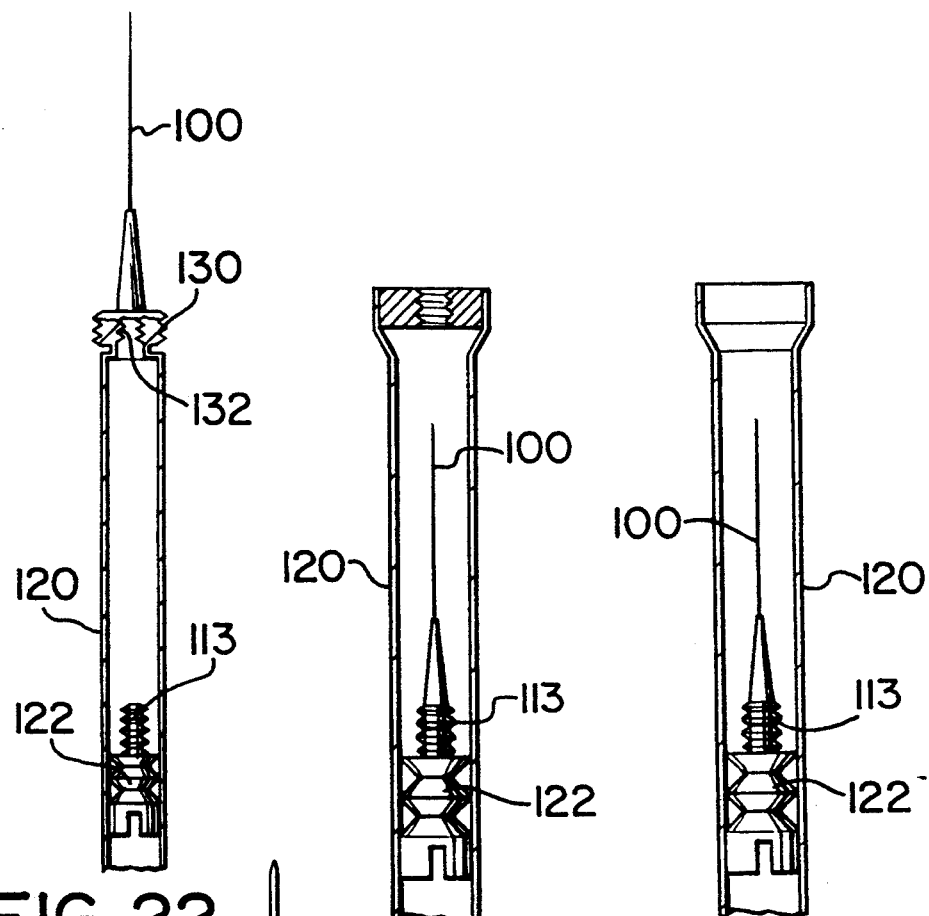
FIG. 22　FIG. 23　FIG. 24
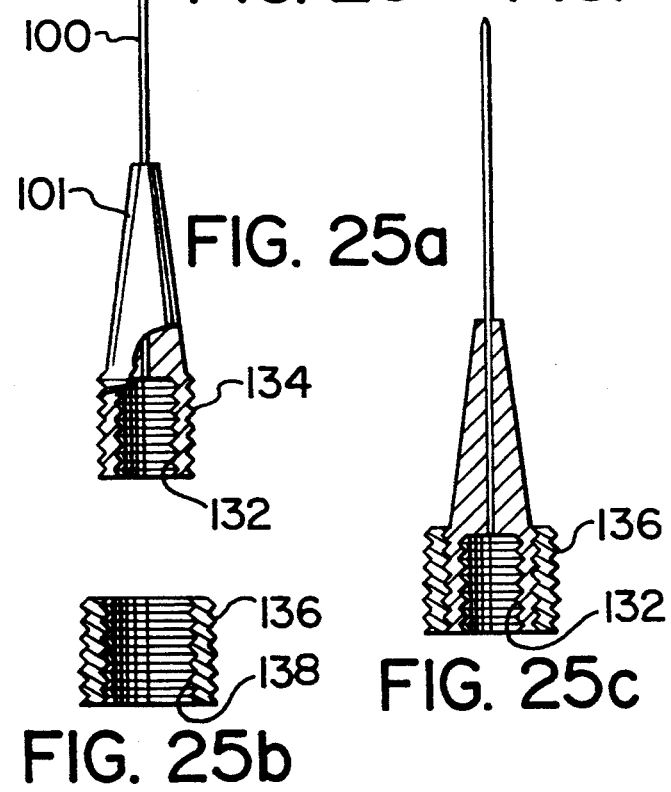
FIG. 25a
FIG. 25b
FIG. 25c

SAFETY SLEEVE FOR DENTAL SYRINGE

FIELD OF THE INVENTION

This invention relates to a safety dental syringe which before and after use protects the needle from exposure. More particularly, this invention pertains to a safety sleeve for a conventional dental syringe wherein after the syringe is used, an overlying sleeve surrounding the barrel of the syringe is extended so that the exposed used needle of the syringe is shielded by the sleeve.

BACKGROUND OF THE INVENTION

Needle stick injury is one of the most common occupational health hazards among healthcare professionals. Those involved in both the dental and medical professions are constantly at risk of dangerous patient-to-staff transmission of AIDS, hepatitis-B and other blood borne diseases from a contaminated needle.

In recent years, with the increase in dangerous communicable diseases, and particularly the growth of the fatal disease known as AIDS (acquired immune deficiency syndrome), it has become critical to eliminate the incidence of needlestick injuries to personnel in the medical profession, and elsewhere, due to contaminated needles of used syringes. There is a constant risk to the medical profession of contracting the disease of an infected patient by being scratched or pricked from the contaminated needle of a used syringe.

A number of designs of syringes which include features for protecting the exposed needle after use of the syringe have been developed and patented in recent years. The following patents are exemplary and not exhaustive.

U.S. Pat. No. 4,655,751, granted Apr. 7, 1987, Harbaugh, discloses a syringe which has a concentric protective shell over the barrel of the syringe. The shell is spaced outwardly from the barrel of the syringe and is slidable between a first needle-exposing position and a second needle-covering position. The shell has windows or a grid to permit viewing of the barrel of the syringe. A number of spacer ears on the barrel's outer surface permit the shell to be temporarily locked into mating pockets with the barrel.

U.S. Pat. No. 4,631,057, granted Dec. 23, 1986, Sampson, discloses an apparatus for injecting a substance into a human or animal. The apparatus includes a body, a needle coupled to the body, and a needle guard mounted on the body for movement from a retracted position in which the guard does not shield the needle to an extended position in which the guard shields the needle. The needle guard can be releasable retained in the retracted position and locked in the extended position. Locking of the needle guard is accomplished by interlocking members carried by the needle guard and by a collar mounted on the body.

U.S. Pat. No. 4,573,976, granted Mar. 4, 1986, Sampson, protects a syringe design which has a needle guard mounted on the body of the syringe, the guard being extendible so that it obstructs access to the point of the needle. The guard can be retracted over the barrel of the syringe to expose the point of the needle. Interlocking members on the body and the guard permit the guard to be releasably locked in the retracted or the extended position.

U.S. Pat. No. 4,425,120, granted Jan. 10, 1984, Sampson, discloses a hypodermic syringe comprising a barrel, a needle coupled to the barrel, and a needle guard mounted on the barrel for movement between an extended position in which the guard shields the needle, and a retracted position in which the guard does not shield the needle. The guard can be locked in either the extended or the retracted position. Locking of the guard is accomplished by a track on the internal surface of the guard and a track engaging member on the barrel.

U.S. Pat. No. 4,859,182, Nerli, discloses a dental syringe of the type having a beak for dispensing fluids into an oral cavity. The syringe comprises a sheath, the sheath being a form fitted, generally elongated tube or cylinder adapted to substantially fit over and cover the beak. The sheath is removably attached to the beak, and provides a substantially sterile outer-covering for the beak. The sheath has an open end and a terminal end having an aperture to allow a fluid to be dispensed from the beak and the sheath. The aperture is located near a discharge orifice of the beak through which the fluid is dispensed. The tip is located at the terminal end of the sheath, the tip and the sheath providing a substantially sterile outer-covering for the beak and the discharge orifice. The tip has a valve coincident with the discharge orifice. The valve allows the fluid to be dispensed from the beak and the tip. The valve substantially prevents contaminants from entering or being drawn into the beak through the discharge orifice.

U.S. Pat. No. 4,826,490, Byrne et al., discloses a safety device for a hypodermic needle. Byrne discloses a disposable non-reusable hypodermic needle assembly comprising: a needle support housing having a connector formation for removable attachment with the apparatus; a hypodermic needle supported by the housing for communication with the apparatus by way of the formation, one end portion of the needle projects from the housing remotely from the formation, and a sheath surrounding the housing and mounted thereon for movement in the longitudinal direction of the needle from a first position nearer to the formation and in which first position the needle one end portion is exposed, to a second position further from the formation and in which second position the needle end is enclosed within the sheath.

U.S. Pat. No. 4,907,968, Elsner, discloses a dental syringe shield or prophylactic which has a removable disposable dental syringe shield for placement over and in proximate contact with the nozzle of a dental syringe. The design includes an elongated cylindrical portion for fitting over the nozzle of the dental syringe and a barrel portion for fitting over the nozzle securing means of the dental syringe. The design also includes a backsplash collar shield, which fits over the nozzle portion and abuts the front of the base portion of the dental syringe.

U.S. Pat. No. 4,898,590, Andors, discloses a syringe comprising: a barrel including longitudinal walls defining an elongate chamber therein for receiving a cartridge; a first, elongate opening defined within the longitudinal walls through which a cartridge may be inserted into the chamber; a second opening defined within the longitudinal walls of the barrel, the second opening in opposing relation to the first elongate opening; and a sleeve slidably mounted to the barrel. The sleeve includes a first elongate opening and a second opening; the second sleeve opening being in opposing relation to the first elongate sleeve opening, the sleeve is movable to a position with respect to the barrel such that the first and second sleeve openings are substantially in register with the first and second barrel openings. The design includes means for retaining the sleeve upon the barrel.

U.S. Pat. No. 4,915,702, Haber et al. discloses a shielded safety syringe comprising an inner syringe cylinder having proximal and distal ends, a hypodermic needle supported at and extending outwardly from the distal end, and an outer protective sleeve having proximal and distal ends. The outer sleeve coaxially alignes with an axially advanceable relative to the inner cylinder from a retracted position, where the needle projects outwardly through an opening in the distal end of the sleeve, to an extended position, where the needle is located within and completely surrounded by the sleeve. A first groove is formed in the inner cylinder and locking means are pivotally interconnected with the outer sleeve and rotatable between unlocked and locked conditions, the locking means rotated to the locked condition for receipt within the groove formed in the inner cylinder when the outer sleeve is advanced axially from the retracted to the extended position relative to the inner cylinder.

Patent Cooperation Treaty, international publication no. WO 90/00073 dated 11 Jan. 1990, discloses a single-use injection needle, in particular for dental applications. The syringe comprises a handle including a piston and a support part for a sleeve having an interlocking structure through which the piston extends. The syringe also comprises a syringe body having a tubular end with an inter-locking structure cooperating with that of the sleeve of the handle. The shape is adapted to interlock with the sleeve, and a protecting shell having a locking section capable of covering the tubular end and the sleeve so that they are locked in their interlocking position. The protective shell is adapted for sliding along the syringe body between two extreme positions, i.e. a forward position where it totally covers the injection needle and a pulled-back position where it frees it and covers the interlocked tubular end and sleeve.

SUMMARY OF THE INVENTION

This invention relates to a safety shield for a dental syringe which after use protects the used needle from exposure and permits ready disposal. More particularly, this invention pertains to a shield for a dental syringe wherein after the syringe is used, an overlying sleeve surrounding the barrel of the syringe is extended and in doing so, engages the shoulder of the needle assembly. The sleeve is then rotated relative to the barrel allowing the needle to be unscrewed and subsequently become firmly suspended within the sleeve. The encased needle is immediately rendered harmless and may be disposed of safely. The inventions is primarily intended for use with a conventional dental syringe. No modification, re-tooling, engineering or structural changes are necessary to the dental syringe, which is conventional.

The invention pertains to a needle and sleeve assembly useful for use in association with a dental syringe comprising a hollow barrel, a piston, and an anaesthetic ampule cavity therein, comprising: (a) a hollow elongated sleeve, having openings at each end thereof; and (b) a hollow housing base which supports at one end thereof an injection needle, and at the other end thereof, an ampule penetrating needle, the exterior of the housing base being adapted to slidably engage with the hollow interior of the sleeve.

In the assembly, the interior of the sleeve can have formed therein at least one longitudinally extending ridge, which is adapted to engage with a longitudinally extending groove in the exterior of the needle housing. The interior of the sleeve can also have formed therein at least one longitudinally extending groove which is adapted to engage with a protrusion on the exterior of the needle housing. The housing can have a groove which has formed therein a pocket, and a spline formed in the interior of the sleeve. The spline can have formed therein a nipple which is adapted to engage with the pocket.

In the assembly, the sleeve can have at least two longitudinal splines in the interior thereof, and the housing can have at least two matching grooves in the exterior of the housing, adapted to engage with the splines of the sleeve. The exterior of the housing can have at least two protrusions thereon, the protrusions being adapted to mate with two longitudinally extending grooves in the interior of the sleeve. The grooves of the sleeve can have formed at one end thereof, recesses which are adapted to receive protrusions on the exterior of the housing, and semi-lock the protrusions into place. The recesses can have formed at a position between the recess and the longitudinal grooves, a constriction which yieldingly permits the protrusion to reversibly move from the groove to the recess and from the recess to the groove.

The invention relates also to a needle housing and sleeve assembly adapted for use with a conventional dental syringe comprising: (a) a hollow elongated sleeve, adapted to fit over the barrel of the dental syringe; (b) a cap releasably attached at one end of the sleeve; (c) a dual-needle and housing assembly fitted releasably with the interior of the end of the sleeve opposite the cap; and (d) a cap releasably fitted over the needle and housing assembly.

In the assembly, the sleeve can have formed in the interior thereof, at least one longitudinally extending spline which is adapted to slidably engage with a corresponding groove formed in the exterior of the needle assembly housing. The groove in the exterior of the housing can have formed therein a stop means which prohibits sliding of the sleeve over the housing assembly beyond a pre-determined position. The sleeve can have formed therein at least one longitudinally extending groove, and the needle housing has formed in the exterior surface thereof at least one matching projection, the projection being adapted to slidably engage in the groove in the interior of the sleeve.

The exterior of the housing can have formed therein adjacent grooves, one forming a full lock position, and the second forming a semi-lock position.

The invention is also directed to a dental syringe comprising: (a) a hollow barrel; (b) a handle movable piston adapted to reciprocate within the barrel; (c) an anaesthetic ampule cavity at one end of the barrel in line with the piston; (d) means for enabling a double pointed dental needle to be affixed to one end of the syringe, whereby one pointed end of the needle penetrates into the interior of the ampule and the other pointed end extends from the end of the syringe; and (e) a plunger positioned in the interior of the ampule, said plunger when moved by the piston in the direction of the needle, pumping anaesthetic from the ampule through the needle, and engaging the needle at the end of the travel, said plunger when moved by the piston away from the needle, withdrawing the needle into the interior of the ampule.

An end of the piston can be adapted with means for engaging the plunger so that the plunger and needle can be withdrawn into the interior of the ampule after the anaesthetic is expelled from the interior of the ampule. The double pointed needle can be secured to the end of the dental syringe by threads, and the plunger can engage the needle assembly by rotating the plunger and piston.

The double pointed needle can have a collar at the mid-section thereof, the collar being adapted to engage with a shoulder, which is adapted to engage the needle end of the dental syringe. The plunger can have formed in one end thereof thread means which are adapted to engage the collar means, and formed at the opposite end of the plunger engagement means which enable the piston to engage the plunger, and move the plunger forwardly and rearwardly within the interior of the ampule, and rotate the plunger clockwise or counter-clockwise.

The ampule can have formed in one end thereof, a plunger and key combination, and in the opposite end thereof, a seal means which seals anaesthetic within the ampule, the seal means engaging one end of the double pointed needle when the anaesthetic is discharged from the ampule, thereby enabling the needle and the seal to be withdrawn into the interior of the ampule by withdrawing the piston and plunger which has engaged the seal.

The invention also pertains to an anaesthetic ampule for use with a dental syringe, comprising: (a) a hollow cylindrical ampule casing; (b) a plunger means enclosed in the ampule casing, the plunger means having at one end thereof an engagement means; and (c) an ampule cap at one end of the ampule casing, the ampule cap having a needle protruding from the end thereof, the ampule cap being adapted to engage with the needle end of a dental syringe, the ampule cap which is adapted to be engaged by the engagement means of the plunger and to be attached from the ampule casing and withdrawn into the interior of the ampule by withdrawal of the plunger means.

The plunger engagement means of the ampule can be a male thread. The engagement means of the ampule cap can be a female thread. The dental syringe and needle end engagement means of the ampule cap can be a thread which is adapted to engage a corresponding thread of a dental syringe. The dental syringe needle end engagement means of the ampule cap can be a male thread which is adapted to engage a female thread of a dental syringe.

The needle can have at the base thereof a housing which has a thread on the exterior thereof, adapted to engage with the ampule cap, said housing having a thread on the interior thereof, a thread adapted to engage with a thread formed on the plunger means.

The ampule and needle can be enclosed in a protective casing. The needle can be encased in a needle cover. The needle cover can have in one end thereof resilient means into which the sharp end of the needle can be embedded. The needle cover and ampule can be encased in a hollow sleeve, with removable caps enclosing each end of the sleeve.

An assembly comprising: (a) a hollow cylindrical casing; (b) a needle housing with an injection needle at one end, and an ampule puncturing needle at the opposite end, enclosed in the casing; (c) an anaesthetic ampule enclosed in the casing; (d) a removable top cap at one end of the casing; and (e) a removable bottom cap at the opposite end of the casing.

DRAWINGS

In drawings which depict specific embodiments of the invention, but which should not be construed as restricting or limiting the scope of the invention in any way:

FIG. 1 illustrates a front perspective view of a typical dental syringe;

FIG. 2 illustrates a front view of a typical dual-needle assembly used by a dentist in the conventional hypodermic syringe illustrated in FIG. 1;

FIG. 3 illustrates a front, partial section view of a safety sleeve suitable for fitting over the barrel of a dental syringe as illustrated in FIG. 1;

FIG. 6 illustrates a partial section view of the safety sleeve withdrawn from the barrel of the dental syringe, and including in the interior thereof the needle assembly;

FIG. 7 illustrates a partial perspective view of the needle housing including grooves formed in the exterior of the needle housing;

FIG. 8 illustrates an end view of the safety sleeve, showing locking nipples extending into the interior thereof around the circumference of the safety sleeve;

FIG. 9 illustrates an alternative embodiment of the needle assembly, including projections extending on the circumference of the needle assembly, matching with the grooves in the interior of the safety sleeve;

FIG. 10 illustrates an alternative embodiment of safety sleeve, including grooves formed in the interior of the sleeve;

FIG. 11 illustrates a perspective view of a collar adapted to fit over a needle housing;

FIG. 12 illustrates a side section view of the collar illustrated in FIG. 11 fitted over a needle housing;

FIG. 13 illustrates a side partial section view of a safety sleeve fitted on a hypodermic syringe, and a collar at the end of the sleeve fitted over the base of the needle housing;

FIG. 14 illustrates a side partial section view of a safety sleeve including a top cap, a bottom cap, and a needle assembly held in the interior of the safety sleeve;

FIG. 22 illustrates a front view of an embodiment of ampule with an ampule cap and needle;

FIG. 23 illustrates a front view of an ampule with the needle withdrawn into the interior of the ampule;

FIG. 24 illustrates a front view of an alternative embodiment of ampule with the needle withdrawn into the interior of the ampule;

FIGS. 25a, 25b and 25c illustrate in succession a front view of a needle and needle housing with threads which engage with threads of an ampule cap, to form the embodiment illustrated in FIG. 25c;

DETAILED DESCRIPTION OF SPECIFIC EMBODIMENTS OF THE INVENTION

Figure 4:
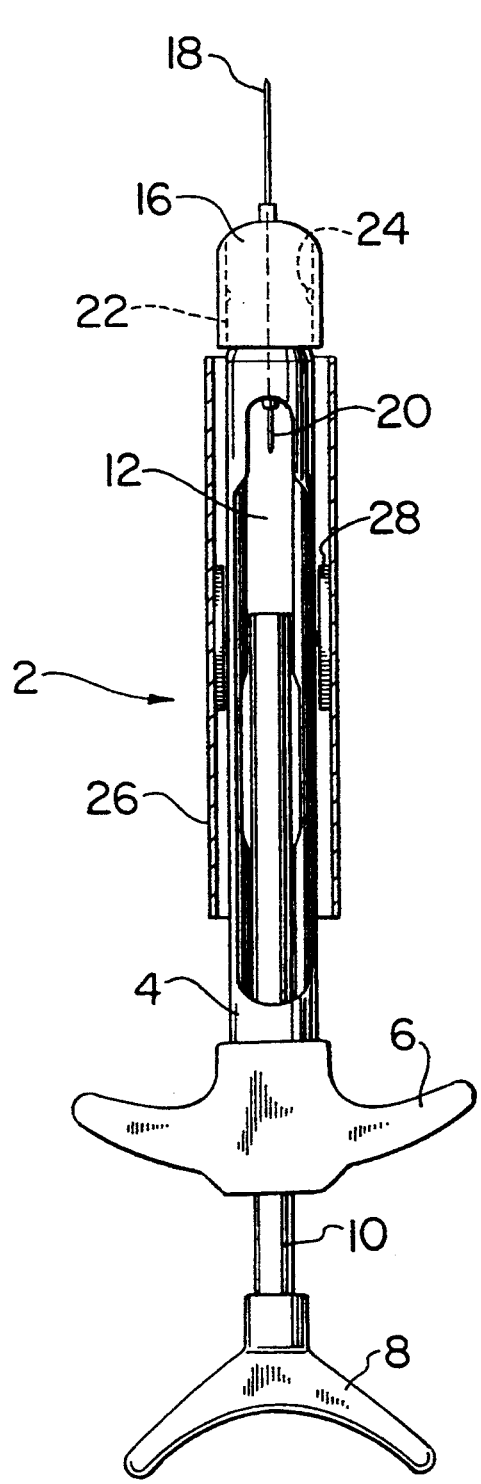
FIG. 4 illustrates a front view of a dental syringe with the safety sleeve as illustrated in FIG. 3, fitted over the barrel of the syringe, and the needle assembly as illustrated in FIG. 2, fitted into the end of the syringe.

The disclosed invention is designed to keep physical exposure to the needle point of a dental syringe at an absolute minimum at all times—thereby giving protection to a handler both at the time of the injection and during subsequent disposal of the used needle. The design and function of the safety sleeve ensures that the handler's hands remain behind the needle as it is covered. Proper use of the safety sleeve should eliminate needle stick injuries to dentists and assistants.

The invention pertains to the shoulder of the needle housing which is designed in a manner to be slightly larger in diameter than the diameter of the body of the syringe thus forming a protruding lip at the point where the needle assembly attaches to the body of the syringe. The needle housing is further designed with lateral grooves. Each groove contains a pocket into which a mating nipple (which is designed to protrude from each of the spline built into the inside of the safety sleeve) will drop, firmly securing the safety sleeve to the needle housing. This locking action takes place when the sleeve is pushed forward (away from the user). In this configuration, the sleeve is rotated, relative to the barrel of the syringe, thus unscrewing the complete needle assembly from the syringe and suspending it securely within the safety sleeve. The sleeve is then fully extended until it disengages from the barrel of the syringe. The sleeve, containing the needle, can now be disposed of safely.

A detailed discussion of specific embodiments of the invention follows in relation to the drawings. Referring to the drawings, FIG. 1 illustrates a front perspective view of a typical dental syringe. The dental syringe 2 is constructed to have a barrel 4, to which are attached a pair of figure grips 6. Inserted into the interior of the hollow barrel is a piston 10 which has at the end thereof a thumb grip 8. The cavity 12 formed between the end of the piston 10 opposite the thumb grip 8, and a portion of the barrel 4 is designed to hold a conventional anaesthetic ampule. The ampule contains an anaesthetic such as Novocaine. At the end of the barrel 4 opposite finger grip 6, there is positioned a male thread needle base which is adapted to receive the female threads inside the housing of a typical double needle used with a dental syringe.

FIG. 2 illustrates a front view of a typical dual-needle assembly used by a dentist in a conventional hypodermic syringe 2 illustrated in FIG. 1. As seen in FIG. 2, the typical dual-needle assembly consists of a hollow needle housing 16, which has formed in the interior thereof female threads adapted to fit with male threads on needle base 14 of the dental syringe 4. The housing has at one end thereof an injection needle 18, which the dentist uses to penetrate into the appropriate nerves in a patient's mouth in order to "freeze" the gum prior to performing dental work on the patient's teeth. At the opposite end, there is an ampule needle 20.

In the conventional case, the dentist screws housing 16 over needle base 14, whereupon, ampule needle 20 penetrates into an end of the ampule which is positioned inside ampule cavity 12. The end of the typical ampule is constructed of rubber so that it is seals the ampule, but can be easily penetrated by the ampule needle 20. Once the ampule needle 20 has penetrated into the interior of the ampule, the dentist can inject anaesthetic through needle 18 by depressing thumb grip 8. The depiction of needle housing 16 is not entirely conventional because, as illustrated in FIG. 2, the exterior of the housing 16 has formed therein a set of vertically extending housing grooves 22. The grooves 22 have formed therein, about midway along the length of the groove 22, appropriate circular pockets 24.

FIG. 3 illustrates a front, partial section view of a safety sleeve 26 which is suitable for fitting over the barrel of a dental syringe as illustrated in FIG. 1, and a needle housing 16, as fitted over needle base 14. Safety sleeve 26 is constructed to have a generally cylindrical configuration, and is hollow. Formed in the interior of the sleeve 26 are a series of interior splines 28, oriented in parallel around the internal circumference of the sleeve 26. The splines 28 are adapted to fit within and slide along respective housing grooves 22 of needle housing 16, when it is screwed onto needle base 14 of the dental syringe 2. Each of the vertical spline 28 has formed thereon at an appropriate point along its length a nipple 30. The nipples 30 are designed to slide into pockets 24 of the housing grooves 22 of the needle assembly, and thereby create a stop position. The combination of the nipples 30 and the pockets 24 prevents the sleeve 26 from being slid entirely off the housing 16, thereby exposing needle 18.

FIG. 4 illustrates a front view of a dental syringe with the safety sleeve 26 as illustrated in FIG. 3, fitted over the barrel 4 of the syringe 2, and the needle assembly as illustrated in FIG. 2, screwed onto the end of the syringe 2. As seen in FIG. 4, the sleeve 26 is in a retracted position, that is, the sleeve is moved in the direction of the finger grips 6, so as to fully expose the needle housing 16, grooves 22, pockets 24, and injection needle 18. While not shown in FIG. 4, the anaesthetic ampule is positioned in cavity 12, and has been penetrated by ampule needle 20. In the configuration illustrated in FIG. 4, the dental syringe 2 is ready for use by the dentist.

Figure 5:
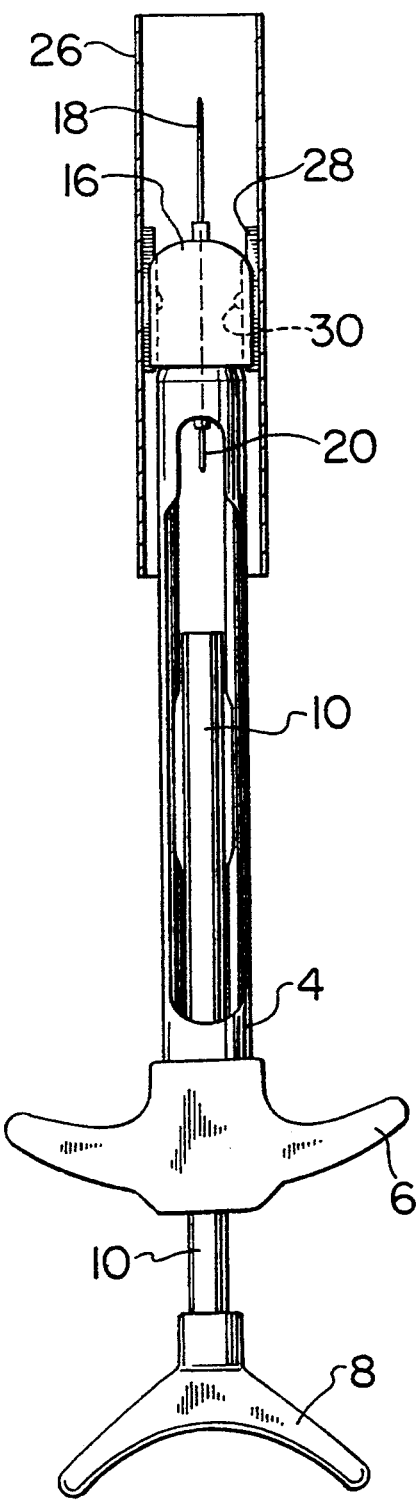
FIG. 5 illustrates a front view of the safety sleeve, as illustrated in FIG. 3, moved to an extended position on the dental syringe so that it covers the needle assembly.

FIG. 5 illustrates a front view of the safety sleeve 26 moved to an extended position over the dental syringe 2 so that it covers the needle assembly. As seen in FIG. 5, splines 28 slide through housing grooves 22 to the point that the nipples 30 fit in pockets 24. The dentist slides sleeve 28 to the needle 18 covering position after he has used the needle to inject anaesthetic into the jaw or gum of the patient. In this position, and since spline 28 fit in grooves 22, the dentist can unscrew housing 16 from needle base 14, and then dispose of the housing 16, needle 18 and ampule needle 20 assembly. It will be noted that when the sleeve 26 is in the extended position, the sleeve 26 is still long enough to cover both the injection needle 18 and the ampule needle 20. Thus, it is entirely safe to dispose of the entire assembly, without running the risk of having the dentist, or a dental assistant, or some other person, accidentally suffer a needle stick injury from either injection needle 18 or ampule needle 20. The ampule is disposed of along with the sleeve 26 and needles 18 and 20.

FIG. 6 illustrates a partial section view of the safety sleeve 26 withdrawn from the barrel 4 of the dental syringe 2, and including in the interior thereof the injection needle 18, the housing 16, and the ampule needle 20. This is the portion that is disposed of without danger of having either needle 18 or needle 20 exposed.

FIG. 7 illustrates a perspective view of the needle housing 16, with a plurality of housing grooves 22 disposed around the circumference of the housing 16. The pockets 24, which are formed in respective grooves 22, are also visible.

FIG. 8 illustrates an end view of the safety sleeve 26, showing the spline 28, dispose around the interior circumference at special locations. The locations correspond with the locations of the grooves 22 in housing 16, as illustrated in FIG. 7. FIG. 8 also shows the nipples 30 formed in the radial interiors of the respective sleeve spline 28. The nipples 30, as mentioned previously, are adapted to fit snugly in pockets 24 and in grooves 22 of housing 16.

FIG. 9 illustrates an alternative embodiment of a needle assembly. This assembly includes a needle housing 32, which has formed at one end thereof injection needle 18 and ampule needle 20. However, in this case, needle housing 32 has around the circumference thereof a series of projections 34. These projections 34, have a similar function as housing grooves 22, in the needle housing embodiment illustrated in FIG. 2.

FIG. 10 illustrates an alternative embodiment of a safety sleeve 36, which has formed in the interior surface thereof a parallel series of linearly extending grooves 38. These grooves 38 are positioned so that they match with projections 34 on needle housing 32 as illustrated in FIG. 9. Thus, when the housing 32 is fitted inside sleeve 36, the projections 34 slide into grooves 38, thereby enabling sleeve 36 to be slid in an axial direction relative to housing 32. The alternative embodiment of sleeve 36 has an semi-locking position facility. The ends of the grooves 38 have formed therein recess 40, extending at right angles to the grooves 38. The housing 32 can therefore be semi-locked into position relative to sleeve 36 by pushing projections 34 into recess 40 by twisting the sleeve 36 slightly relative to housing 32. This is done when housing 32 has been screwed onto needle base 14 of syringe 2.

Between groove 38 and recess 40, there is formed a slight constriction 42. This constriction 42 slightly retards the entry of projection 34 into recess 40. Constriction 42 therefore provides a pre-semi-locked facility because it ensures that projection 34 does not slide into recess 40 unless the dentist specifically wants to place the sleeve 36 in the semi-locked position. When projections 34 are moved into recess 40, then injection needle 18 is retracted into the interior of the sleeve 36, and the combination can be disposed of without fear of having the handler exposed to the protruding needle 18.

FIG. 11 illustrates a perspective view of a collar which can be fitted over the housing of a standard dual-needle housing in order to adapt the housing so that a sleeve can be placed over the housing and the collar. As seen in FIG. 11, the collar 44 is formed in a hollow cylindrical shape, and is adapted to fit over needle housing 16 of a standard dual-needle housing. Grooves 46 are arranged so that they meet with a sleeve 26, as illustrated in FIG. 3. Splines 28 of sleeve 26 slide in grooves 46. The collar 44 can also have formed their end pockets which receive nipples 30 of sleeve 26 to provide a locking feature.

FIG. 12 illustrates a side section view of the collar 44 fitted over housing 16 of a typical dentist's dual-needle. The collar 44 can be formed to have a slight lip 45, formed around the bottom circumference thereof. Lip 45 snaps over the end of housing 16, and holds collar 44 in place.

FIG. 13 illustrates a side partial section view of a conventional hypodermic syringe with collar 44 fitted over needle housing 43. As seen in FIG. 13, the sleeve 26 is in a retracted position over the barrel of the syringe, thereby exposing needle 47. Collar 44, therefore, enables a standard hypodermic syringe to be adapted to utilize the protective slidable sleeve 26, according to the invention.

FIG. 14 illustrates a side partial section view of a safety sleeve including a top cap, a bottom cap, and a needle housing. As seen in FIG. 14, the assembly includes a sleeve 48, which has formed in the interior thereof a series of splines 50 extending axially along a good portion of the length of sleeve 48. Nipples 51 are also visible in FIG. 14. Enclosing the sleeve 48 at the bottom end thereof is a bottom cap 52. At the top end of the sleeve 48, there is fitted a needle housing 16, with injection needle 18, and ampule needle 20. While not readily visible in FIG. 14, housing 16 has formed in the interior surface thereof grooves 22 and pockets 24, as illustrated previously in FIG. 3. Fitted over the housing 16 and injection needle 18 is a top cap 54.

This assembly can be sold as a unit, complete with a anaesthetic ampule inside the sleeve 48. This unit can be sold directly to the dentist, who probably already has on hand one or more conventional stainless steel dental syringes as illustrated in FIG. 1. In order to use the assembly, the dentist simply unscrews the bottom cap 52, and removes the anaesthetic ampule, if one is sold with the assembly. The dentist then places that ampule or another ampule into cavity 12 of the syringe 2 and places the sleeve 48 over the barrel 4 of the syringe 2 and rotates the sleeve 48 so as to screw the female threads which are in the interior of housing 16 onto the male threads of needle base 14 (see FIG. 1). Once the housing 16 is securely screwed over base 14, ampule penetration needle 20 has totally penetrated into the interior of the ampule in the cavity 12 through the membrane in the end of the ampule. At that point, the dentist removes top cap 54, thereby exposing injection needle 18. The combination is then ready for use on the patient. Once the injection is completed, the dentist extends the sleeve over the the exposed needle 18, and the unit can be discarded.

The advantage of the assembly illustrated in FIG. 14 is that it neatly fits with existing techniques and equipment used in the dental profession, while at the same time providing the dentist and associated personnel with protection from exposed needles. Currently, the dentist typically receives a needle housing 16, with a cap similar to top cap 54, mounted over the injection needle 18. Likewise, a bottom cap fits over ampule needle 20. With the existing system, the dentist removes the bottom cap and screws the housing 16 onto the base 14, thereby having the ampule needle 20 penetrate the ampule. Then, the dentist removes the top cap in order to expose the injection needle 18.

In the assembly as illustrated in FIG. 14, much the same sequence of actions is followed. However, the advantage of the assembly shown in FIG. 14 is that it includes a safety sleeve 48, which can be extended over injection needle 18 after use, in order to enable the assembly to be discarded without exposing injection needle 18 or ampule needle 20 to the handler.

Figure 15:
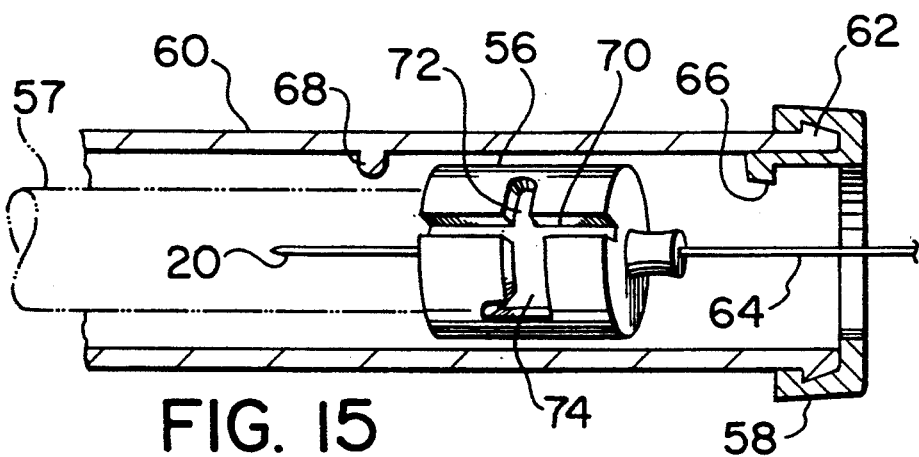
FIG. 15 represents a partial section, partial perspective view of a dental syringe with a protective sleeve thereover, and an end cap on the sleeve.

FIG. 15 illustrates a partial section side view of a safety sleeve including a top collar cap, and a needle housing. As seen in FIG. 15, the dental syringe 57 is fitted at its end with an embossed needle ferrule 56. The syringe 57 and ferrule 56 are enclosed by a sleeve 60 which has an end collar 58 at the needle end thereof. The end collar 58 fits over the end of the sleeve 60 by a snap lip 62, formed at the end of sleeve 60. An upper pin 66 serves two purposes. First, it forms a key which discourages detachment of the end collar 58. It also serves as a male projection which is adapted to slide in main linear groove 70 in the exterior of the ferrule 56. The sleeve 60 is also fitted with an internal lower pin 68. This lower pin 68 discourages removal of the sleeve 60 from the ferrule 56. The sleeve 60 slides back and forth on the ferrule 56 by having lower pin 68 engaged in main groove 70. The exterior surface of ferrule 56 also has a semi-lock groove 72 formed to one side of groove 70, which can be engaged by rotating the sleeve 60 relative to the ferrule 56 and syringe 57, and a main lock groove 74 on the other side of groove 70, which can be engaged by rotating the sleeve 60 in the opposite direction relative to ferrule 56 and syringe 57.

The embodiment illustrated in FIG. 15 has the advantage that there are semi-lock and main lock positions which can be engaged by the dentist or assistant in order to discourage movement of the sleeve 60 relative to the syringe 57 and ferrule 56. In one respect, the embodiment illustrated in FIG. 15 is the alternative of the embodiment of the collar and needle combination discussed previously in association with FIGS. 9 and 10.

Figure 18:
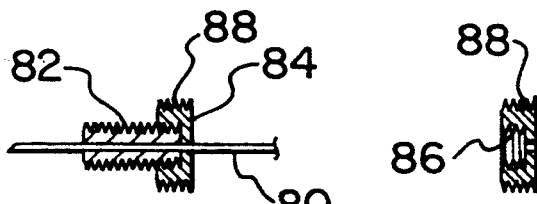
FIG. 18 represents a side view of a threaded shoulder engaged over a threaded collar of a dental needle.
Figure 17:
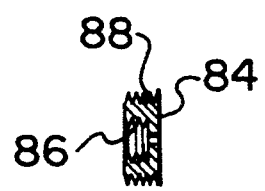
FIG. 17 represents a side view of a threaded shoulder for a dental needle.
Figure 16:
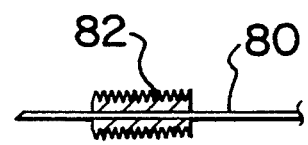
FIG. 16 represents a side view of a two-pointed dental needle with a threaded collar about the mid-section of the needle.

FIGS. 16, 17 and 18 illustrate an embodiment of the invention wherein the needle is equipped with a collar and a shoulder adapted to mate with the end of a dental syringe. As seen in FIG. 16, the two-pointed needle 80 has a male thread collar 82 around its mid-section. FIG. 17 illustrates a side section view of a shoulder 84 which is of a general cup-shape, with a female thread 86 on the interior circumference thereof, and a male thread 88 on the exterior wall thereof. The female thread 86 is adapted to engage with the male thread on the exterior of the collar 82. FIG. 18 illustrates the shoulder 84 and the collar 82 engaged on needle 80.

Figure 19:
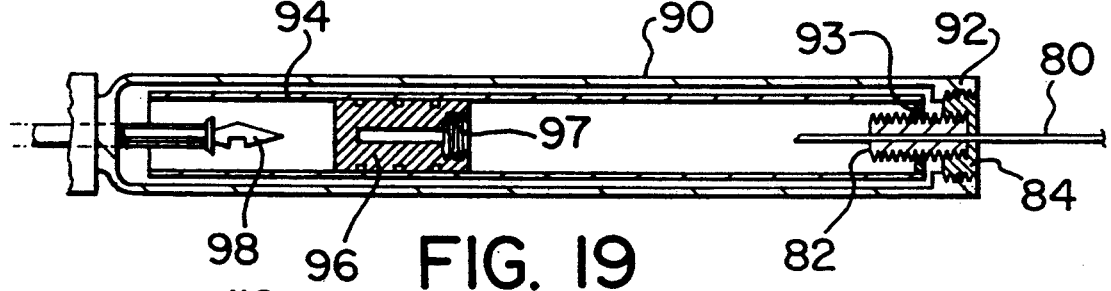
FIG. 19 illustrates a side partial section view of a dental syringe with an ampule within the syringe, adapted for use with the needle collar combination illustrated in FIGS. 16, 17 and 18.

FIG. 19 illustrates a side partial section view of a dental syringe (of a design marketed by Health Co. Corp.) which has a dental syringe barrel 90 with a female thread 92 at the needle end of the barrel 90. An anaesthetic containing ampule 94 is fitted inside the syringe barrel 90 in a conventional manner. The ampule 94 has at one end thereof a plunger 96, and at the opposite end, a seal membrane 93. When needle 80, with collar 84, is screwed into threads 92, the needle 80, and part of the collar 82, penetrates seal membrane 93. At the opposite end, the dental syringe 90 is equipped with a barbed hook 98 which, when advanced, that is, to the right as seen in FIG. 19, penetrates into the exterior of plunger 96, which is usually formed of resilient rubber or plastic. This action pushes the plunger 96 in the direction of the needle 80 and expels the anaesthetic through needle 80. When the anaesthetic is fully pumped through needle 80, the plunger 96 meets with collar 82. The dentist can then rotate the plunger 96, with female threads 97 formed therein, to engage the male threads at the end of collar 82. Normally, the threads would be right hand threads. Once the threads 82 and 97 are engaged, the dentist continues to rotate the plunger 96, which causes the threads 82 to disengage from shoulder 84. Once fully disengaged, the dentist can then withdraw the plunger 96, together with the collar 82, and seal 93 and needle 80, into the interior of the empty ampule 94. Once the collar 82, seal 93 and needle 80 is fully withdrawn into the interior of ampule 94, the barbed hook 98 is withdrawn from plunger 96 and the ampule 94, together with the enclosed needle 80 and collar 82, can be discarded without any danger of puncture by contact with needle 80.

Figure 20:
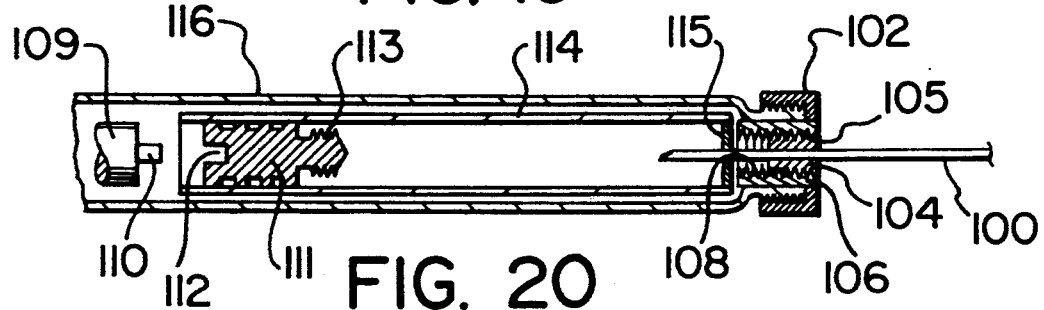
FIG. 20 illustrates a side partial section view of an alternative embodiment of a dental syringe with an ampule therein, and a needle-collar-cap combination.

FIG. 20 illustrates a side partial section view of an alternative design of needle 100, which is also adapted to be withdrawn into the interior of anaesthetic ampule 114. As seen in FIG. 20, the needle 100 is housed within a hollow needle cap 102, which has a female thread on the interior wall thereof. A needle collar 104, with a male thread thereon, encircles the mid-section of needle 100. A collar sleeve 106 is positioned between the needle cap 102, and the needle collar 104. Needle cap 102 is screwed onto the end of dental syringe housing 116. In doing so, the needle 100 punctures seal 115 and penetrates into the interior of ampule 114. The opposite end of the ampule 114 is equipped with a plunger 111, which has formed at the end thereof, a projection with male threads 113. The push rod 109 of the syringe handle proximate to plunger 111 is equipped with a push rod key 110. This push rod key 110 engages in plunger key receptacle 112, which is formed in the external end of plunger 111. This key 110 can be shaped according to any suitable design, for instance, a simple linear ridge 110 which fits in a linear groove 112, similar to a screwdriver fitting into a slot at the head of a screw. If more contact surfaces are required, the combination can be X-shaped, star-shaped, or square-shaped. The designs can be similar to the various combinations of Phillips and Robertson screws and screwdrivers that are available on the marketplace. The dentist pushes the push rod 109 in the direction of the needle 100 and the cap 102, and thereby causes plunger 111 to pump the anaesthetic in the ampule 114 out through needle 100. After the anaesthetic is fully pumped out of the ampule 114, the dentist then rotates the push rod 109, key 110, slot 112 combination which causes male threads 113 to penetrate membrane seal 115 and engage the female threads 108 in the interior of collar sleeve 106. By continuing to rotate the push rod 109 after threads 113, 108 are fully engaged, the threads 105 of needle collar 104 (which are in the opposite direction), disengage from collar sleeve 106. Once fully disengaged, the needle collar 104, the seal 115 and the needle 100 can be withdrawn into the interior of the ampule 114, and the combination discarded without fear of contact with the needle 100.

Figure 21:
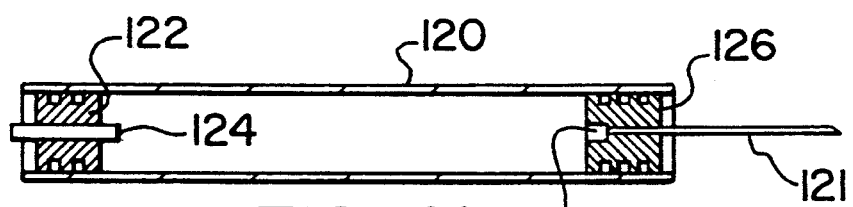
FIG. 21 illustrates an alternative embodiment of an ampule with a plunger at one end and a seal at the opposite end.

FIG. 21 illustrates a side partial section view of a further embodiment of an ampule 120 which is adapted so that the needle 121 can be withdrawn into the interior of the ampule 120 after use. One end of the ampule 120 is equipped with a plunger 122, which has a plastic key 124 penetrating through it. The opposite end of the ampule 120 has a seal 126 which has a key receptacle 128 formed therein. When the needle 121 penetrates into the interior of seal 126, the seal 126 grips the end of the needle 121. Subsequently, when the dentist pushes the plunger 122 towards the needle 121, seal 126, in order to pump the contents of the ampule 120 through the needle 121, the plunger 122 eventually meets with seal 126 so that plastic key 124 engages with key receptacle 128. The seal 126 is designed so that it can be readily withdrawn into the interior of ampule 120, after the anaesthetic is pumped out. The seal 126 is prevented from escaping the interior of ampule 120 by the conventional syringe housing (not shown) and suction created by the filled ampule 120 if the seal 126 attempts to escape. However, when plunger 122 and key 124 contact the seal 126, and key receptacle 128, after the anaesthetic is exhausted, a connection is made which is sufficiently strong that seal 126, with needle 121, can be withdrawn into the interior of ampule 120 by withdrawing plunger 122. Once the needle 121 is fully withdrawn into the interior of ampule 120, the ampule and the used needle 121 can be discarded without fear of puncture by the exposed pointed end of needle 121.

FIG. 22 illustrates a front view of an embodiment of ampule with an ampule cap and needle. As seen in FIG. 22, the ampule 120 is fitted at its top with an ampule cap 130, which has male threads around the circumference. These threads are adapted to screw into a conventional dental syringe (not shown) which has had the adapter coupling removed. The internal female threads 132 are adapted to be engaged with the male threads 113 at the top end of plunger 122. The injection needle 100 is engaged at its base with the top of ampule cap 130. After use, that is, the plunger 122 has been fully advanced through the interior of the ampule, thereby forcing the anaesthetic through needle 100, male threads 113 are rotated into female threads 132, thereby enabling the needle housing and needle 100 to be withdrawn into the interior of the ampule 120 by withdrawing the plunger 122.

FIG. 23 illustrates a front view of an ampule with the needle withdrawn into the interior of the ampule. As seen in FIG. 23, the plunger 122 has been withdrawn after male threads 113 are engaged so that the needle 100 and housing can be withdrawn into the interior of the ampule 120. FIG. 24 illustrates a front view of an alternative embodiment of ampule with the needle withdrawn into the interior of the ampule.

FIGS. 25a, 25b and 25c illustrate in succession a front view of a needle and needle housing with threads which engage with threads of an ampule cap, to form the embodiment illustrated in FIG. 25c. As seen in FIG. 25a, the needle 100 and needle housing 101, have at the base thereof male threads 134 on the exterior, and female threads 132 on the interior. FIG. 25b shows in detail the construction of the threaded ampule cap with male threads 136 on the exterior, and female threads 138 on the interior. When the male threads 134 of the needle housing 101 are screwed into female threads 138 in the ampule cap, the combination illustrated in FIG. 25c is obtained.

Figure 26:
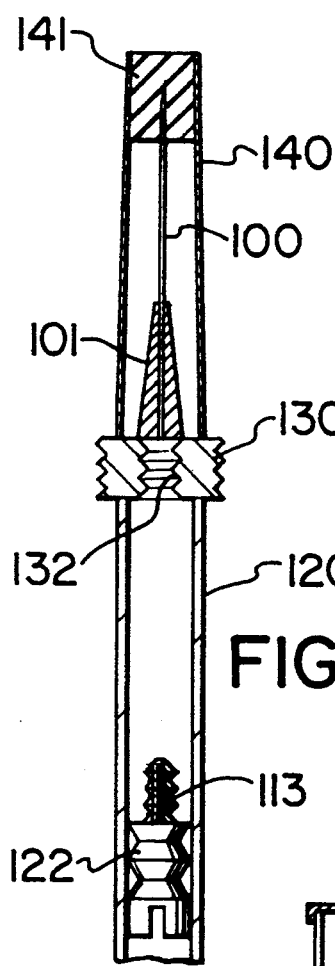
FIG. 26 illustrate a front view of an ampule with ampule cap, needle and needle cover, assembled as a unit for shipping.

FIG. 26 illustrate a front view of an ampule with ampule cap, needle and needle cover, assembled as a unit for shipping. This figure illustrates the needle cover and ampule when sold as a unit in a plastic tube or a bubble pack, or the like. This embodiment does not have the usual soft sealing membrane across the neck of the ampule, but rather, the needle tip is embedded in the rubber, or any other suitable material. This embodiment can be used with a conventional metal dental syringe which has had the needle adapter coupling removed. As seen in FIG. 26, the needle 100, and needle housing 101, are encased in a needle cover 140. The needle cover 140 can have a rubber plug 141 at the top, into which the sharp end of the needle 100 can be embedded in order to maintain a clean needle end. The lower portion of the ampule 120 is the same construction as described previously, with ampule cap 130, covered by the base of the needle cover 140, and plunger 122 and male threads 113 at the top of plunger 122 adapted to engage with female threads 132 of ampule cap 130, when the plunger 122 is fully advanced in the interior of the ampule 120.

Figure 27:
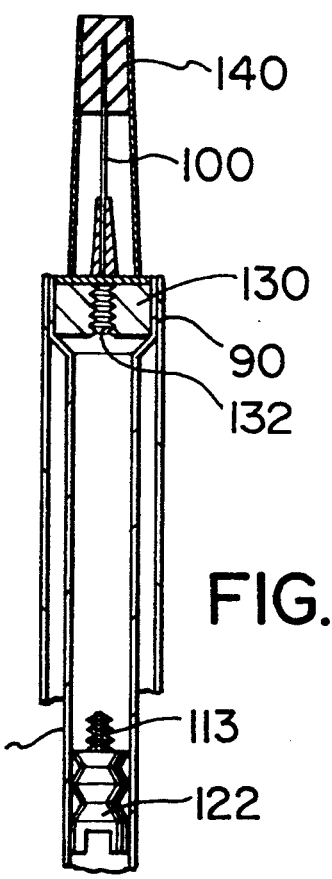
FIG. 27 illustrates a front view of an ampule with ampule cap, needle, and cover inserted in a standard dental syringe.

FIG. 27 illustrates a front view of an ampule with ampule cap, needle, and cover inserted in a standard dental syringe. As seen in FIG. 27, the ampule 120 and needle assembly 100 and 130 is engaged with the top end of the dental syringe 90.

Figure 28:
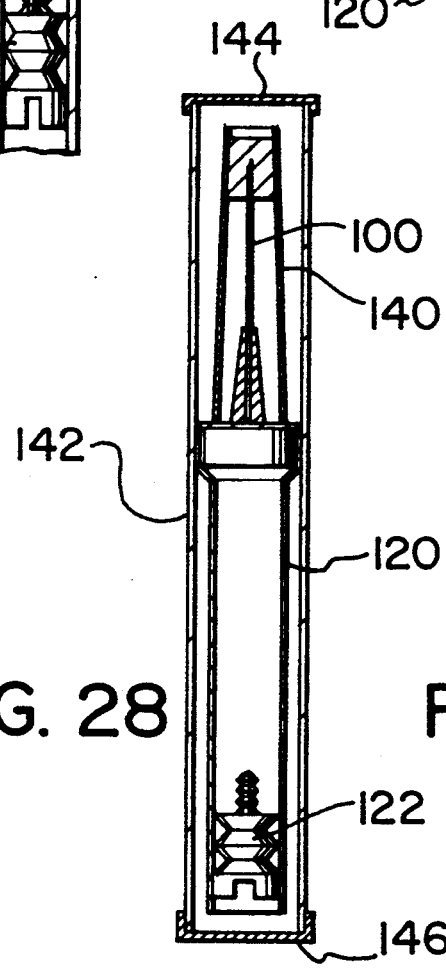
FIG. 28 illustrates a front view of an ampule with needle and cover enclosed in a sleeve package with double caps, for shipping.

FIG. 28 illustrates a front view of an ampule with needle and cover enclosed in a sleeve package with double caps, for shipping. FIG. 28 shows the ampule 120, and needle 100 encased in a sleeve package 142, which is closed at the top end by top cap 144, and closed at the bottom end by bottom cap 146. Needle cover 140, as previously described, covers needle 100. This embodiment represents the package that is assembled and shipped by the manufacturer.

Figure 29:
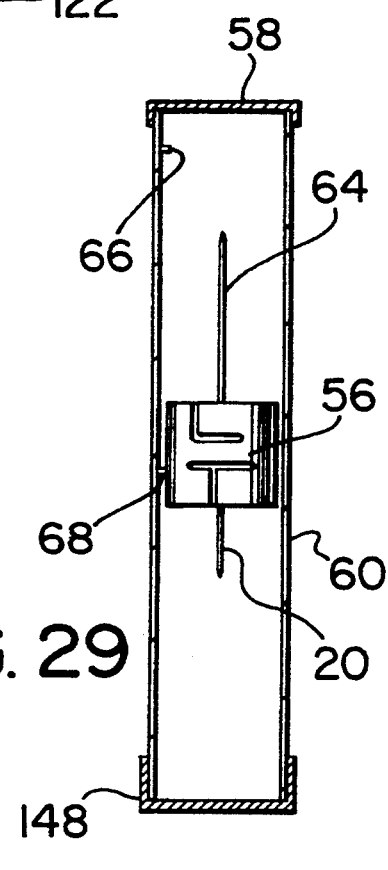
FIG. 29 illustrates a front view of a needle shoulder with needle and ampule needle at either end, encased in a double cap sleeve for shipping.

FIG. 29 illustrates a front view of a needle shoulder with needle and ampule needle at either end, encased in a double cap sleeve for shipping. As seen in FIG. 29, the embossed needle ferrule 56 is encased in sleeve 60, which is closed at the top end by end collar 58, and at the bottom end by bottom cap 148. FIG. 29 also illustrates the injection needle 64 at one end of the ferrule 56, and the ampule needle 20 at the opposite end of ferrule 56. As seen in FIG. 29, ferrule 56 is engaged with lower pin 68 on the sleeve 60. Upper pin 66 is shown at the top interior of sleeve 60.

Figures 30A, 31A:
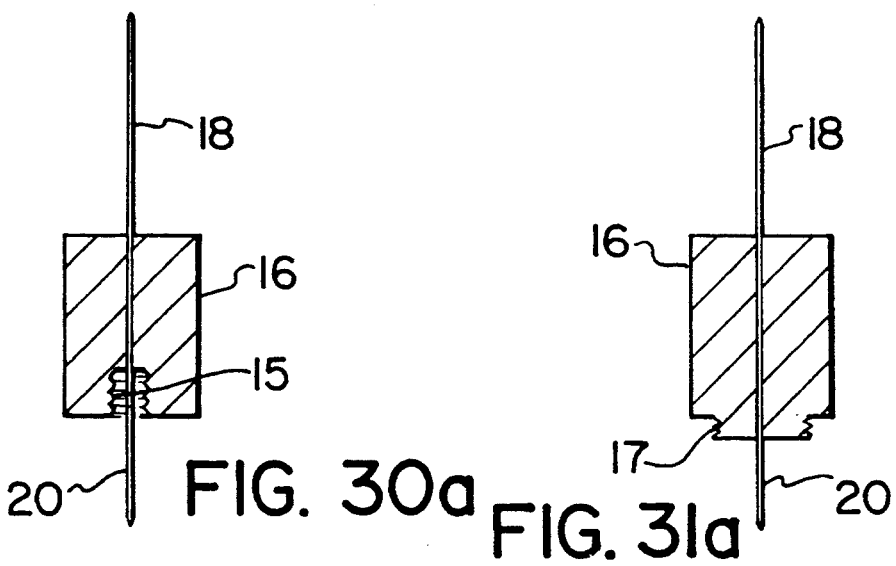
FIGS. 30a and 30b illustrate a front view of an embodiment of a needle housing with female threads adapted to engage the male thread of a standard dental syringe.
FIGS. 31a and 31b illustrate a front view of a needle housing with a male thread adapted to engage with a female thread of a dental syringe.
Figures 30B, 31B:
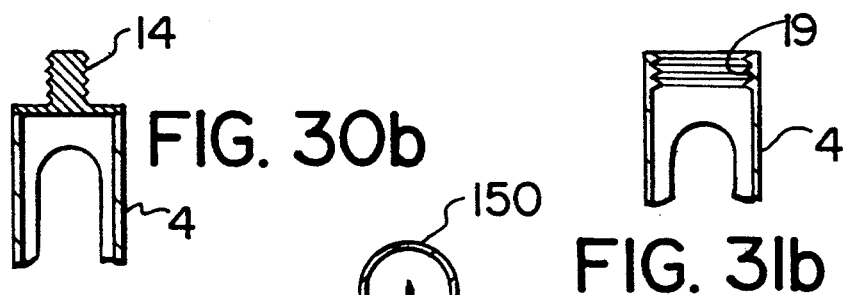

FIGS. 30a and 30b illustrate a front view of an embodiment of needle housing with female thread adapted to engage the male thread of a standard dental syringe. FIG. 30a in particular illustrates needle housing 16, with interior female threads 15 at the base end thereof immediately above ampule needle 20. Female housing threads 15 are adapted to engage with the male needle base housing threads 114 of a conventional metal dental syringe 4 (see FIG. 1). FIG. 31a is similar to FIG. 30a, except that male threads 17 replace female threads 15 at the base of the needle housing 16. The shoulder threads 17 screw into the female interior threads 19 of a conventional dental syringe, as seen in FIG. 31b. A needle adapter coupling is not necessary with this embodiment.

Figure 32:
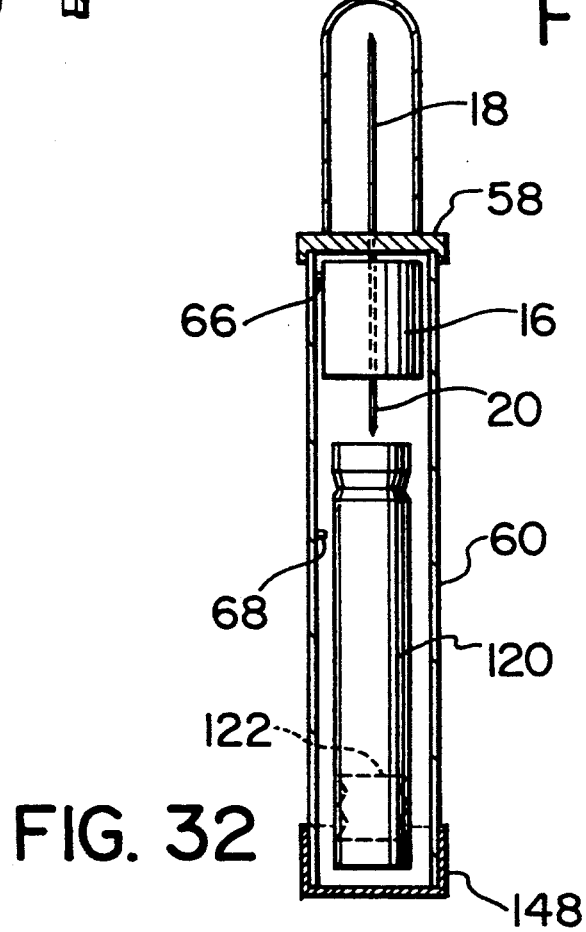
FIG. 32 illustrates a front view of an ampule and needle housing encased in a sleeve, with caps at both ends, and a top cap covering the injection needle for shipping.

FIG. 32 illustrates a front view of an ampule and needle housing encased in a sleeve, with caps at both ends, and a top cap covering the injection needle for shipping. FIG. 32 illustrates an assembly which comprises both a needle housing 16, with injection needle 18, and ampule needle 20, positioned at the top end of sleeve 60, while the ampule 120, with plunger 122, is located in the lower portion of sleeve 60. The top end of sleeve 60 is closed with collar 58, and a bell-shaped top cap 150, which protects needle 18. The base of sleeve 60 is enclosed with bottom cap 148. It should be noted that if the length of the sleeve 60 proves to be too short to house the needle assembly and the ampule, the bottom cap 148 can be lengthened to accommodate the situation. To use this configuration, the dentist removes the bottom cap 148, and the ampule 120 is loaded into the dental syringe barrel 4. The safety sleeve 60 is placed over the exterior of the syringe barrel 4, and the needle housing 16 is screwed into the top end of the metal dental syringe. The needle top cap 150 is then removed, thereby exposing injection needle 18 ready for use. The plunger 122 is depressed by the plunger of the dental syringe, thereby causing ampule needle 20 to penetrate the top end of ampule 120. The anaesthetic enclosed in the ampule 120 is then expelled through injection needle 18. After use, the plunger 122 is withdrawn, which in turn causes needle housing 16 to release from upper pin 66, and retract to lower pin 68. In this way, needle 18 is withdrawn into the interior of the sleeve 60. The sleeve 60, with the ampule 120, and the withdrawn needle 18, can then be disposed of. The assembly depicted in FIG. 32 is the package that is assembled by the manufacturer and shipped to the wholesaler or distributor for use by the dentist.

Use and Function of Safety Syringe

The dentist loads the syringe with an ampule of anaesthetic, pulls the safety sleeve back over the barrel and screws the dual ended needle into the syringe. The syringe is now ready for injection of anaesthetic into a patient's gums.

On completion of the injection (and as the needle is being withdrawn from the patient's mouth), the dentist holds the safety sleeve and draws the needle back into the sleeve thereby effectively covering the needle tip. The pulling motion is continued, which causes the spline of the safety sleeve to engage with the grooves of the needle housing, thereby locking the two together. The sleeve is then rotated, which unscrews the needle, leaving it encased within the sleeve. The sleeve is fully extended, disengaging it from the body of the syringe and is now ready for disposal. By adopting this post injection methodology, the dentist and dental assistants are protected from accidental needle stick injuries. It should be noted that both of the handler's hands remain behind the needle at all times. It is never necessary to place a hand ahead of the needle, such as is the case when a conventional cap is placed over a conventional exposed needle.

Basic Engineering

Various methods may be adopted to "lock" the safety sleeve to the needle housing and to "hold" the sleeve to the barrel of the syringe while the sleeve is in the retracted position.

The foregoing illustrations and explanations relate to a transparent plastic encasement (sleeve) which slides upon the barrel of the syringe. The sleeve contains internal lateral splines, each having a protruding nipple. The splines are designed to engage with female lateral grooves which are designed into the shoulder of the needle housing. Each groove contains a pocket which receives the protruding nipple of the spline, thus fixedly securing the safety sleeve to the needle assembly. In this configuration, the user is able to unscrew the needle assembly which is now securely encased within the safety sleeve.

The secondary function of the interior splines, and the nipples protruding from the splines, is to "hold" the sleeve firmly to the barrel while the sleeve is in the retracted position. Further, the nipple's contact with the barrel of the syringe allows the sleeve to travel upon the barrel of the syringe while the sleeve is placed in the retracted and extended positions. Care must be taken to regulate fit to allow the sleeve to travel over the barrel of the syringe using a "user" comfortable amount of pressure, yet not so great as to cause "stickiness". If additional stability is required to hold the sleeve on the syringe, additional nipples may be added to the spline.

The invention works equally well if the splines and grooves are reversed. The invention can be used with metal or plastic syringes, whether they are the reusable, or disposable types.

Use of Collar

An alternative method of suspending the needle assembly within the sleeve is to adapt a collar which locks onto the needle housing. The collar has the same properties and exhibits the same functions as the needle housing described above in that the collar is grooved and overlaps the barrel of the syringe and is designed to mate with the safety sleeve in the same manner as described previously. The collar "conversion" is designed for use with needle assemblies being manufactured to current specifications.

Hypodermic Syringes

The foregoing inventions can also be readily designed for application to hypodermic syringes now in use. No modification, retooling, engineering or structural changes are necessary to the syringe. When used with a disposable hypodermic syringe, it is not necessary to unscrew the needle housing from the barrel of the syringe. In this locked position, the entire unit (syringe and sleeve) may be disposed of safely. The encased needle may also be unscrewed before disposal.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. A dental syringe and ampule combination comprising:
    (a) a hollow elongated barrel having a first end and a second end and a longitudinal axis and an opening in the side thereof for receiving and holding an ampule;
    (b) a slidable handle having a first end and a second end, the first end of the handle protruding from the first end of the barrel and being located outside the first end of the barrel, the second end of the handle being located inside the barrel;

(c) a handle moveable piston having a first end proximate to and connected to the second end of the handle and a second end of the piston opposite the first end of the piston, the piston being located and slideably held in the interior of the hollow barrel the piston reciprocating along the longitudinal axis within the interior of the barrel;

(d) an anaesthetic ampule cavity formed at the second end of the interior of the barrel in longitudinal axis alignment with and adjacent to the second end of the piston, the cavity being connected to the opening;

(e) a hollow needle with first and second pointed ends and having at threaded needle mounting between the first and second pointed ends, the needle being located at the second end of the barrel with the second pointed end of the needle protruding from the second end of the barrel;

(f) a hollow cylindrical anaesthetic ampule casing mounted in the ampule cavity, the ampule casing having a first end proximate to the second end of the piston and a second end proximate to the first pointed end of the double pointed needle and the second end of the barrel;

(g) threaded means for enabling the needle mounting to be affixed to the second end of the barrel whereby the first pointed end of the needle penetrates into the interior of the ampule cavity and the ampule casing and the second pointed end of the needle extends from the second end of the barrel in a direction opposite to the handle and the first pointed end;

(h) a slideable plunger means having a first end and a second end enclosed in the first end of the ampule casing, the first end of the plunger means being releasably engaged by engagement means on the second end of the piston, the second end of the plunger means having threads for releasably engaging an ampule cap at the second end of the ampule casing, the ampule cap being proximate to the first end of the needle, the ampule cap being penetrated by the first end of the needle and releasably engaging by threads with the second end of the barrel, the ampule cap engaging by threads with the second end of the plunger means and being detached from the ampule casing and withdrawn into the interior of the ampule casing by withdrawal of the plunger means; said plunger means being positioned in the interior of the ampule casing when engaged by the second end of the piston and moved by the piston in the direction of the second end of the needle protruding from the second end of the barrel, thereby pumping anaesthetic from the interior of the ampule through the needle, and threadedly engaging the first pointed end of the needle and the needle mounting at the end of travel of the piston and the plunger means towards the second end of the barrel, said piston and plunger means when rotated and moved by the piston towards the first end of the barrel away from the second end of the barrel, disengaging the ampule cap and corresponding threads, and the needle mounting, and withdrawing the ampule cap, the threaded mounting and the first and second pointed ends of the needle into the interior of the ampule casing.

2. A dental syringe as claimed in claim 1 wherein the second end of the piston has thereon releasable engagement key means for engaging the first end of the plunger means so that the plunger means and double pointed needle can be withdrawn into the interior of the ampule casing after the anaesthetic is expelled from the interior of the ampule casing.

3. A dental syringe as claimed in claim 2 wherein the double pointed needle and the needle mounting have female threads which are secured to male threads on the second end of the barrel, and the second end of the plunger means has threads which engage corresponding mating threads on the needle mounting when the plunger means an the piston are rotated.

4. A dental syringe as claimed in claim 3 wherein the mounting of the double pointed needle is a collar which is located at the mid-section of the double pointed needle, the collar releasably engaging with the second end of the barrel.

5. A dental syringe as claimed in claim 4 wherein the second end of the plunger means has formed thereon male threads which are adapted to engage the collar, and the plunger means has formed at the first end of the plunger means key engagement means which enable the second end of the piston to releasably engage the first end of the plunger means, and reciprocally move the plunger means axially within the interior of the ampule casing and rotate the plunger means clockwise or counterclockwise about the longitudinal axis.

6. A dental syringe as claimed in claim 5 wherein the ampule has positioned in the first end thereof, a plunger and key combination, and in the second end thereof, a seal means which seals anaesthetic within the ampule, the seal means engaging an ampule interior end of the double pointed needle and when the anaesthetic is discharged from the interior of the ampule through the double pointed needle, the double pointed needle and the seal means are engaged by the second end of the plunger means and are withdrawn into the interior of the ampule by withdrawing the piston and plunger means, the second of which has engaged the seal means.

7. A dental syringe as claimed in claim 1 wherein the mounting of the double pointed needle is a housing which has a thread on the exterior thereof for engagement with a corresponding thread on the ampule cap, said housing having a thread on the interior thereof for engaging with a corresponding thread formed on the second end of the plunger means.

8. A dental syringe as claimed in claim 7 wherein the second end of the double pointed needle is encased in a needle cover which is removed before the syringe is used.

9. A dental syringe as claimed in claim 8 wherein the needle cover has in one end thereof resilient means into which a sharp end of the double pointed needle can be embedded.

10. A dental syringe as claimed in claim 8 wherein the needle cover and ampule are encased in a hollow sleeve, with removable caps enclosing each end of the sleeve.

11. A dental syringe as claimed in claim 7 wherein the ampule and the double pointed needle are enclosed in a protective casing prior to insertion of the ampule in the ampule cavity.

12. A dental syringe as claimed in claim 1 wherein the second end of the piston has thereon a male thread for engaging a corresponding female thread on the first end of the plunger means.

13. A dental syringe as claimed in claim 12 wherein the ampule cap has a female thread for engaging the second end of the plunger means.

14. A dental syringe as claimed in claim 1 wherein the ampule cap has thereon a thread which engages a corresponding thread of the second end of the barrel of the dental syringe.

15. A dental syringe as claimed in claim 1 wherein the ampule cap has thereof a male thread which engages a corresponding female thread on the second end of the barrel of the dental syringe.

* * * * *